United States Patent

Joung et al.

[11] Patent Number: 5,820,765
[45] Date of Patent: Oct. 13, 1998

[54] APPARATUS AND METHOD FOR DISPLAYING THE PURIFYING EFFICIENCY OF THE WATER PURIFIER

[75] Inventors: Geum-Suk Joung; In-Gue Joung, both of Suwon, Rep. of Korea

[73] Assignee: Samsung Electronics Co., Ltd., Suwon, Rep. of Korea

[21] Appl. No.: 735,602

[22] Filed: Oct. 23, 1996

[30] Foreign Application Priority Data

Apr. 17, 1996 [KR] Rep. of Korea ............... 96-11565
Apr. 24, 1996 [KR] Rep. of Korea ............... 96-12750

[51] Int. Cl.$^6$ .................. B01D 17/12; B01D 61/12
[52] U.S. Cl. .................. 210/739; 210/85; 210/96.2; 210/257.2; 324/71.1; 324/439; 340/403; 340/664
[58] Field of Search .................. 210/85, 96.1, 96.2, 210/143, 257.2, 259, 739, 746, 767; 324/439, 449, 71.1; 340/603, 664

[56] References Cited

U.S. PATENT DOCUMENTS

| | | | |
|---|---|---|---|
| 3,838,774 | 10/1974 | Dolan et al. | 210/85 |
| 3,856,676 | 12/1974 | Grimme et al. | 210/96.2 |
| 3,990,066 | 11/1976 | Malmgren | 210/96.2 |
| 4,160,727 | 7/1979 | Harris | 210/257.2 |
| 4,784,763 | 11/1988 | Hambleton et al. | 210/96.2 |
| 4,937,557 | 6/1990 | Tucci et al. | 210/96.2 |
| 5,096,574 | 3/1992 | Birdsong et al. | 210/96.2 |
| 5,362,383 | 11/1994 | Zimmerman et al. | 210/96.2 |
| 5,450,358 | 9/1995 | Seibert et al. | 210/96.2 |
| 5,494,573 | 2/1996 | Schoenmeyr et al. | 210/257.2 |

*Primary Examiner*—Joseph W. Drodge
*Attorney, Agent, or Firm*—Burns, Doane, Swecker & Mathis, L.L.P.

[57] ABSTRACT

This invention relates to an apparatus for displaying the purifying efficiency of a water purifier. The apparatus is adapted to compare the quality of supplied water with that of purified water and then display the result. The apparatus comprises a supply water quality sensing element for sensing an amount of pollutant substances contained in the supplied fresh water and produced water quality sensing element for sensing an amount of pollutant substances contained in purified water that has passed though filters in the purifier. An amplifying unit is included for amplifying weak signals sensed by the sensors. A subtractor receives the signals obtained from the amplifying unit and derives a difference between the amplified signals. A divider is supplied for dividing the output signal from the subtractor by the sensed and amplified signal from the supply water quality sensing element, and an adjusting unit is provided for adjusting erroneous values to obtain the correct results of the subtractor and divider. A control unit derives the purifying efficiency based upon the signal output from the divider and, from the above derived result, outputs a signal indicating the purifying efficiency and the purified state of the purified water. A displaying unit receives the output signal from the control unit via a driving circuit, and displays the purifying efficiency and the purified state.

10 Claims, 6 Drawing Sheets

APPARATUS AND METHOD FOR DISPLAYING THE PURIFYING EFFICIENCY OF THE WATER PURIFIER

BACKGROUND OF THE INVENTION

FIELD OF THE INVENTION

The invention relates to a water purifier for removing noxious pollutant substances contained in fresh water, such as tap water. More particularly, the invention relates to an apparatus for displaying a purifying efficiency, the apparatus being adapted to compare a supplied water with a purified water and then to display the comparison result.

Typically, water purifiers are used to remove noxious pollutant substances contained in fresh water, such as tap water, in order to supply purified water. Purifiers are classified into a natural filtering type, a forced filtering type, an ion exchanging resin type and a reverse osmotic type in accordance with methods for purifying water.

Water purifiers of the reverse osmotic type, which force fresh water to pass through an artificial osmotic membrane (reverse osmotic filter) while applying pressure to the fresh water, can remove heavy metals, bacteria, cancer-causing materials, and the like, contained in the water, thereby purifying the water. Since the reverse osmotic water purifiers can supply pure water containing only dissolved oxygen, they have been used in fields such as super-pioneering scientific industries, medical sciences or cleaning for super-precision electronic elements. Recently, such reverse osmotic water purifiers have widely been used as domestic water purifiers for supplying drinkable water.

Figure 1:
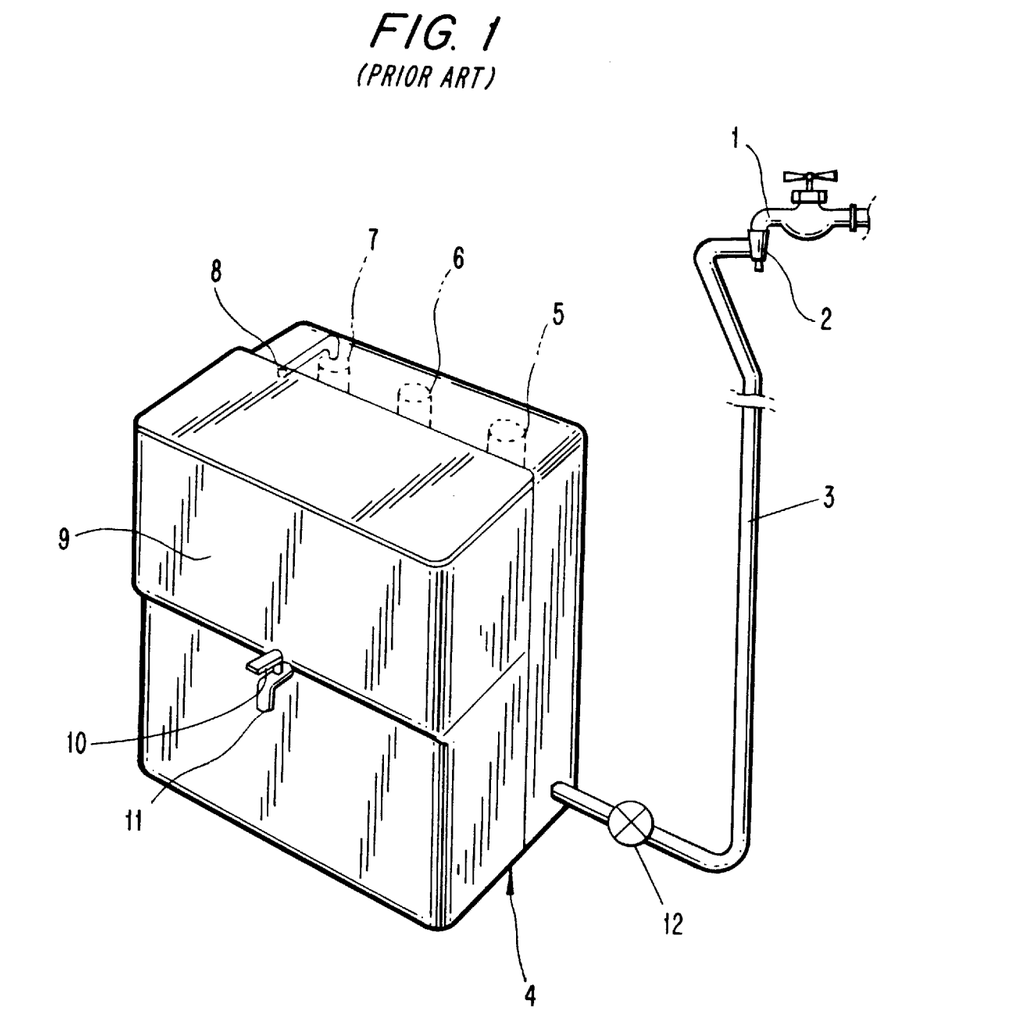
FIG. 1 is a perspective view illustrating the overall construction of a conventional water purifier.

FIG. 1 illustrates a conventional reverse osmotic water purifier having the above-mentioned function. As shown in FIG. 1, the water purifier includes a purifier body 4 which is connected to a faucet 1 via a water supply pipe 3. This water supply pipe 3 is coupled to the faucet 1 by means of an adapter 2. The purifier body 4 is supplied with fresh water such as tap water, from the faucet 1 through the water supply pipe 3. The fresh water introduced into the purifier body 4 passes through a pre-processing filter 5 disposed at the rear portion of the purifier body 4. The pre-processing filter 5 removes various harmful organic chemical materials such as chlorine components and the like from the water passing therethrough. The water emerging from the pre-processing filter 5 then passes through a water supply valve which controls an amount of water supplied. The water from the water supply valve is then introduced into a pressure pump so that it can be pressurized to a certain pressure level. The pressurized water is fed to a membrane filter 6 which includes a plurality of membranes (not shown). While passing through the membranes, the water becomes free of heavy metals, bacteria, cancer-causing materials, and the like, contained therein. The water emerging from the membrane filter 6 then passes through a post-processing filter 7 by which odorous substances, such as noxious gas, are removed from the water.

The water, which has a pleasant taste as it becomes free of odorous substances, such as noxious gas, while passing through the post-processing filter 7, is then fed to a water tank 9 through a water supply port 8.

When the purified water is supplied in the water tank 9, it is determined whether the amount of water contained in the water tank 9 corresponds to a full water level (namely, the maximum water amount requiring to shut off the supply of purified water to the water tank) or an empty water level (namely, a minimum water amount requiring to supply purified water to the water tank).

Where the amount of water contained in the water tank 9 corresponds to the full water level, the supply of purified water to the water tank 9 is shut off. On the other hand, where the amount of water tank 9 corresponds to the empty water level, the water tank 9 is supplied with purified water. In such a manner, the water tank 9 is always stored with a constant amount of purified water.

The purified water stored in the water tank 9 can be discharged through a discharger port 11 by manipulating a water discharge lever 10.

Figure 2:
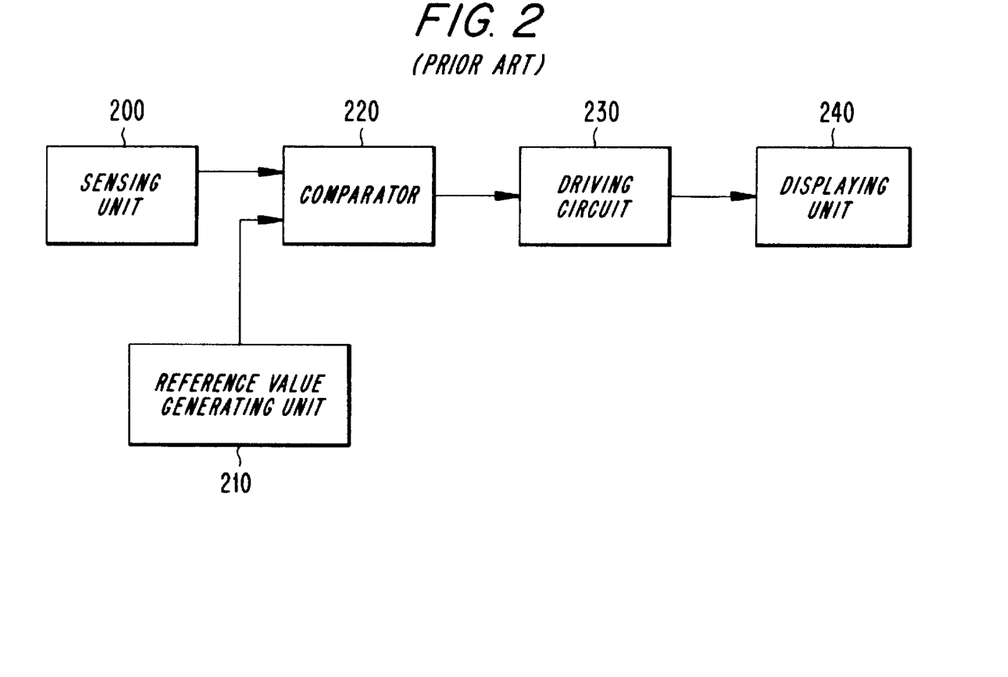
FIG. 2 is a block diagram illustrating a water quality sensing block of a conventional water purifier.
Figure 3:
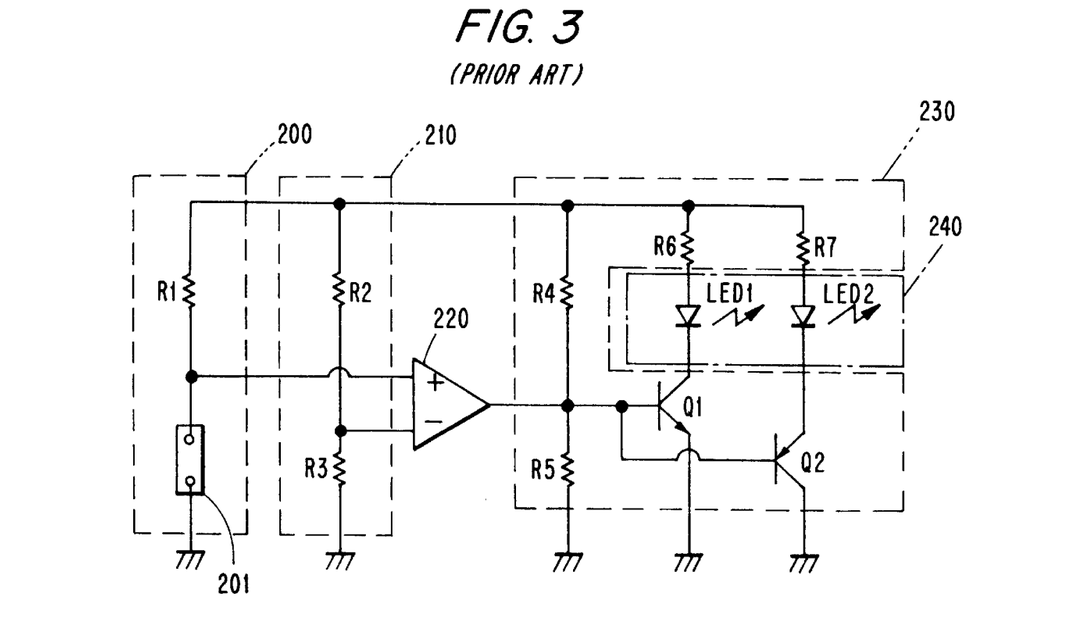
FIG. 3 is a circuit diagram of a water quality sensing block of a conventional water purifier.

The conventional water purifier as described above is also provided with a circuit, as shown in FIGS. 2 and 3, for detecting the quality of the purified water stored in the water tank 9.

As shown in FIGS. 2 and 3, the circuit comprises: sensing means 200 composed of a water quality sensing element 201 having a varying resistance component that operates based upon the amounts of various electrolytes contained in the purified water, and a resistor R1; reference value generating means 210 having two resistors R2 and R3; a comparator 220 having two input terminals of inverting and non-inverting terminals; and a driving circuit 230, wherein each of inverting and non-inverting terminals of the comparator 230 receives an electric potential divided by the resistance of the resistor R1 and the varying resistance of said sensing element 201, and an reference electric potential divided by the resistors R2, R3 of the reference value generating means 210, respectively.

In case that the level of the electric potential input to the non-inverting terminal (+) of the comparator 220 is higher than that of the reference electric potential input to the inverting terminal of the same comparator, the output of the comparator 220 goes to high and then the transistor Q1(npn type) of the driving circuit 230 is turned on, which causes a light emitting diode LED1 of the displaying unit 240 to be activated.

In contrast, in case that the level of the electric potential input to the non-inverting terminal (+) of the comparator 220 is lower than that of the reference electric potential input to the inverting terminal (−) of said comparator, the output of the comparator 220 goes to low, and then, in turn, the transistor Q2(pnp type) of the driving circuit 230 is turned on, thereby causing LED2 of the displaying unit 240 to be activated.

Based upon such a principle, it can be known as to whether the purified state of the water is acceptable or not. Since more contaminants contained in the water cause electric current in the water to flow well, the output of the comparator 220 becomes low, thereby turning on LED2. When the purified state of the water is acceptable, the output of the comparator 220 becomes high, thereby turning on LED1. The state of either LED 1 or LED2 indicates whether the purified state of the water is acceptable or not.

As can be seen from the above conventional approach, it can be only displayed whether the purified state is acceptable or not. Therefore, it is difficult to determine detailed quality levels of the purified water. Because the user doesn't know when the filters should be exchanged for new ones, the reliability for the filters becomes lowered.

SUMMARY OF THE INVENTION

Therefore, it is an object to provide an apparatus for displaying a purifying efficiency of a water purifier which displays the purifying efficiency indicating what amounts of noxious pollutant substances are filtered through the filters, based upon measurements of pollutant substances in the supplied water and purified water, and allows a user to identify when filters should be exchanged for new ones.

The above objects are accomplished using an apparatus for displaying a purifying efficiency of a water purifier. The water purifier includes a pre-processing filter, a membraned filter, and a post-processing filter. A water tank stores the purified water passed through said filters, which water tank comprises supply water quality sensing element for sensing an amount of pollutant substances contained in supplied fresh water; a produced water quality sensing element for sensing the amount of pollutant substances contained in the purified water passed through said filters; amplifying means for amplifying weak signals sensed by the sensors; a subtractor for receiving signals obtained from the respective amplifying means and deriving a difference between the amplified signals; a divider for dividing an output signal from the subtractor by the sensed and amplified signal from the supply water quality sensing element; adjusting means for adjusting erroneous values to obtain the correct results of said subtractor and divider; control means for deriving the purifying efficiency based upon the signal output from the divider and, from the above derived result, outputting a signal indicating the purifying efficiency and the purified state; and displaying means for receiving the output signal from the control means via a driving circuit and displaying the purifying efficiency and the purified state.

BRIEF DESCRIPTION OF THE DRAWINGS

Other objects and aspects of the invention will become apparent from the following description of embodiments with reference to the accompanying drawings in which.

DETAILED DESCRIPTION OF THE PREFERRED EMBODIMENT

Figure 4:
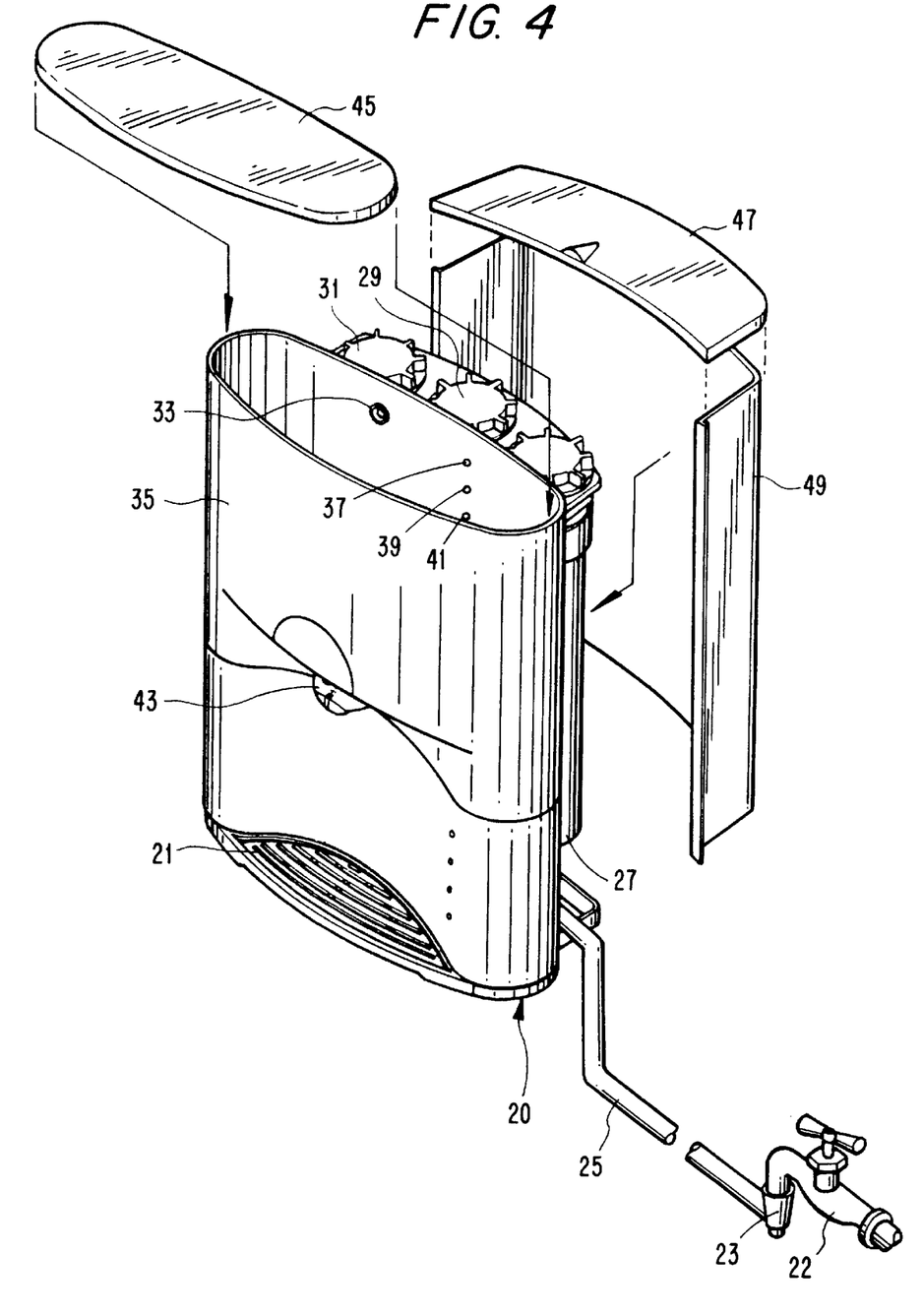
FIG. 4 is an exploded perspective view illustrating a water purifier according to an embodiment of the present invention.

In FIG. 4, reference numeral 20 denotes a body of the water purifier. The purifier body 20 has provided at its front portion a cup receiving portion 21 for receiving a water receptacle such as cup.

At the rear side of the purifier body 20, one end of a water supply pipe 25 is connected to the purifier body 20. The other end of the water supply pipe 25 is connected to a faucet 22 by means of a connecting member 23. In the purifier body 20, a pre-processing filter 27 is disposed. The pre-processing filter 27 is connected to the water supply pipe 25 and is adapted to remove various harmful organic chemical substances such as chlorine components, and the like, from fresh water supplied from the faucet 22.

At one side of the pre-processing filter 27, a membrane filter 29 is disposed which includes a plurality of membranes (not shown) serving to remove heavy metals, bacteria, cancer-causing materials, and the like, contained in the water emerging from the pre-processing filter 27. A post-processing filter 31 is connected to the membrane filter 29 to remove odorous substances, such as noxious gas, contained in the water emerging from the membrane filter 29.

A water tank 35 is separably seated on the purifier body 20. The water tank 35 has a water inlet port 33 to receive and store the water purified by the post-processing filter 31. The water tank 35 also has provided at its inner rear surface, a pair of water level sensors 37 and 39 respectively adapted to sense different amounts of purified water stored in the water tank 35 corresponding to the full and empty water levels.

A water discharge lever 43 is coupled to the front surface of the water tank 35 to discharge the purified water stored in the water tank 35 through a water discharge port (not shown). The water tank 35 is covered at its top portion with an upper cover 45. At the rear side of the upper cover 45, another upper cover 47 is separably coupled to the top portion of the purified body 20. At the rear side of the purifier body 20, a rear cover 49 is also coupled to the purifier body 20.

In FIG. 4, reference numeral 41 denotes sensing electrodes of a pair of water level sensors 37 and 39.

Figure 5:
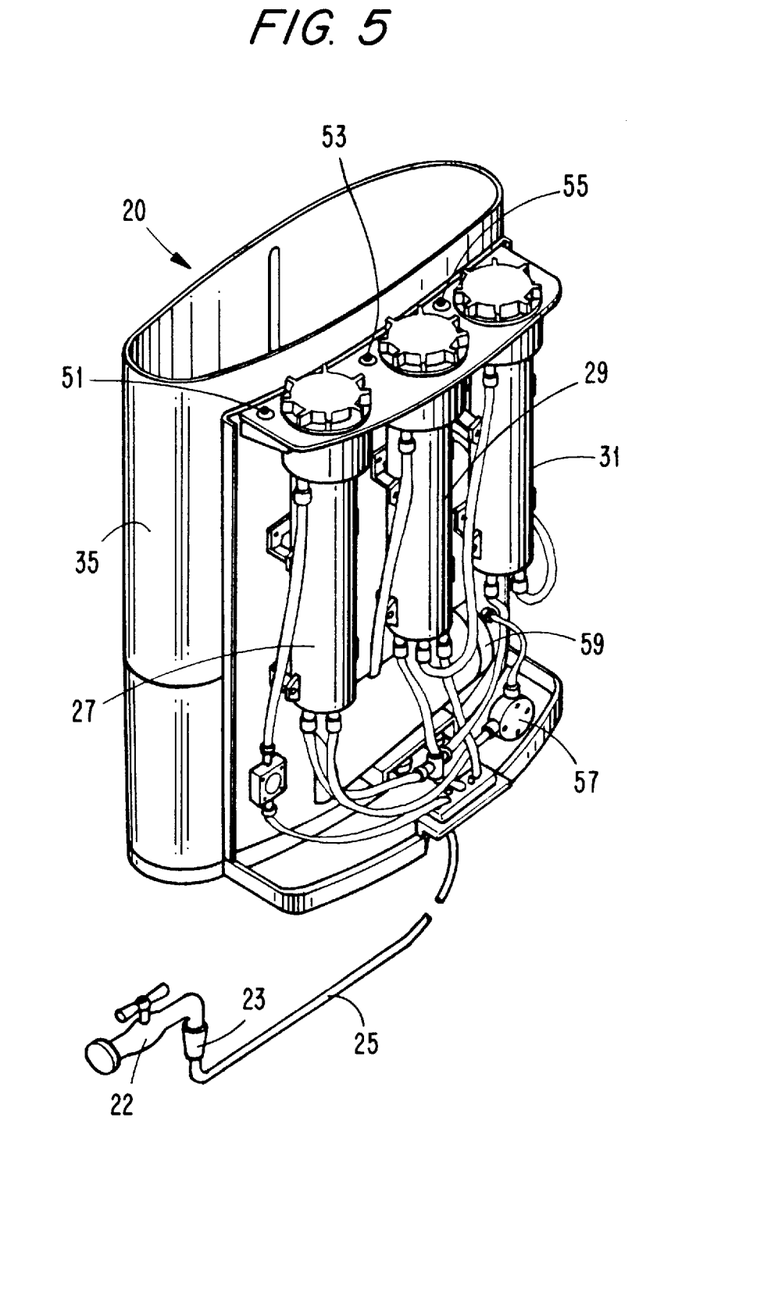
FIG. 5 is a rear perspective view of the water purifier according to an embodiment of the present invention.

As shown in FIG. 5, on upper ends of the pre-processing filter 27, the membrane 29 and the post-processing filter 31 there are provide reset switches 51, 53 and 55 for resetting the time period permitted for use of for each of the filters when the pre-processing filter 27, the membrane 29 and the post-processing filter 31 are exchanged.

Beneath the post-processing filter 31, a water supply valve 57 is disposed, which is connected between the post-processing filter 31 and the water tank 35, as shown in FIG. 5. The water supply valve 57 is opened and closed in accordance with the amount of purified water contained in the water tank 35, namely, the water level of the water tank 35. A pressure pump 59 is connected between the pre-processing filter 27 and the membrane filter 29 to apply pressure to the water emerging from the pre-processing filter 27, thereby feeding the water to the membrane 29 at a certain pressure. Since water under pressure is fed to the membrane filter 29 by the pressure pump 59, it can be purified by the membrane filter 29 in a reverse osmotic manner.

The circuit for displaying the purifying efficiency of the water purifier will be described in detail with reference to FIG. 6 and FIG. 7.

Figure 6:
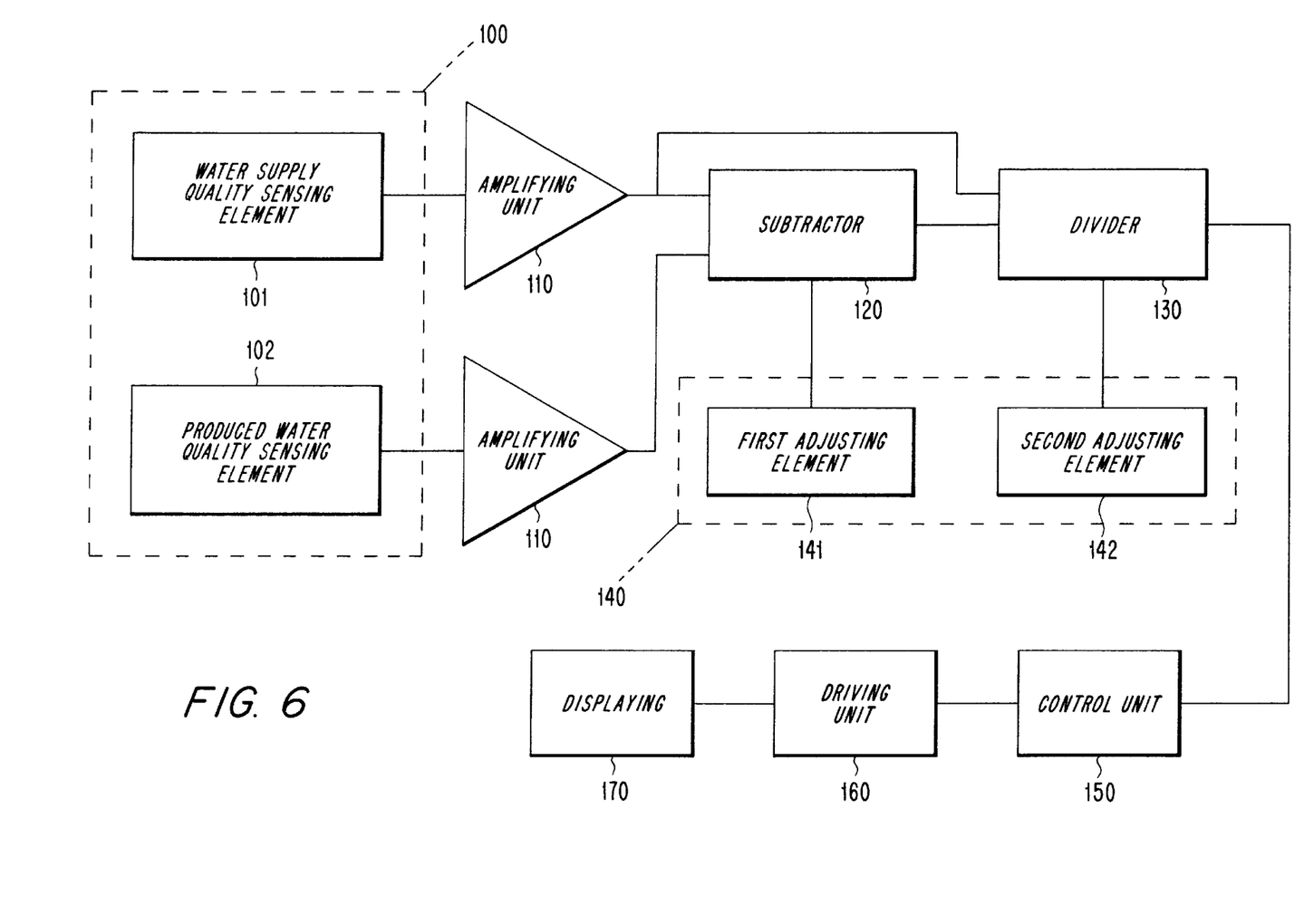
FIG. 6 is an apparatus for displaying the purifying efficiency of the water purifier according to an embodiment of the present invention.

Referring to FIG. 6, the circuit is composed of water quality sensing means 100 having a water supply quality sensing element 101 for sensing the amount of pollutant substances contained in supplied fresh water and a produced water quality sensing element 102 for sensing the amount of pollutant substances contained in the purified water; a pair of amplifying means 110 for amplifying weak signals from the water quality sensing means 100; a subtractor 120 for receiving the signals obtained from the amplifying means and deriving a difference between the amplified signals; a divider 130 for dividing an output signal from the subtractor 120 by the sensed and amplified signal from the amplifying means 110 for ratio calculations; adjusting means 140 having a first adjusting element 141 and a second adjusting element 142, wherein the output signals are adjusted to obtain correct results for the subtractor 120 and divider 130; a microcomputer(hereinafter, referred to as a control means) 150 for deriving the purifying efficiency based upon the signal output from the divider 130 and, from the above derived result, outputting a signal showing a purifying efficiency and a purified state; and a driving circuit 160 for sending the output signal from the control means 150 to displaying means 170 adapted to display the results.

Figure 7:
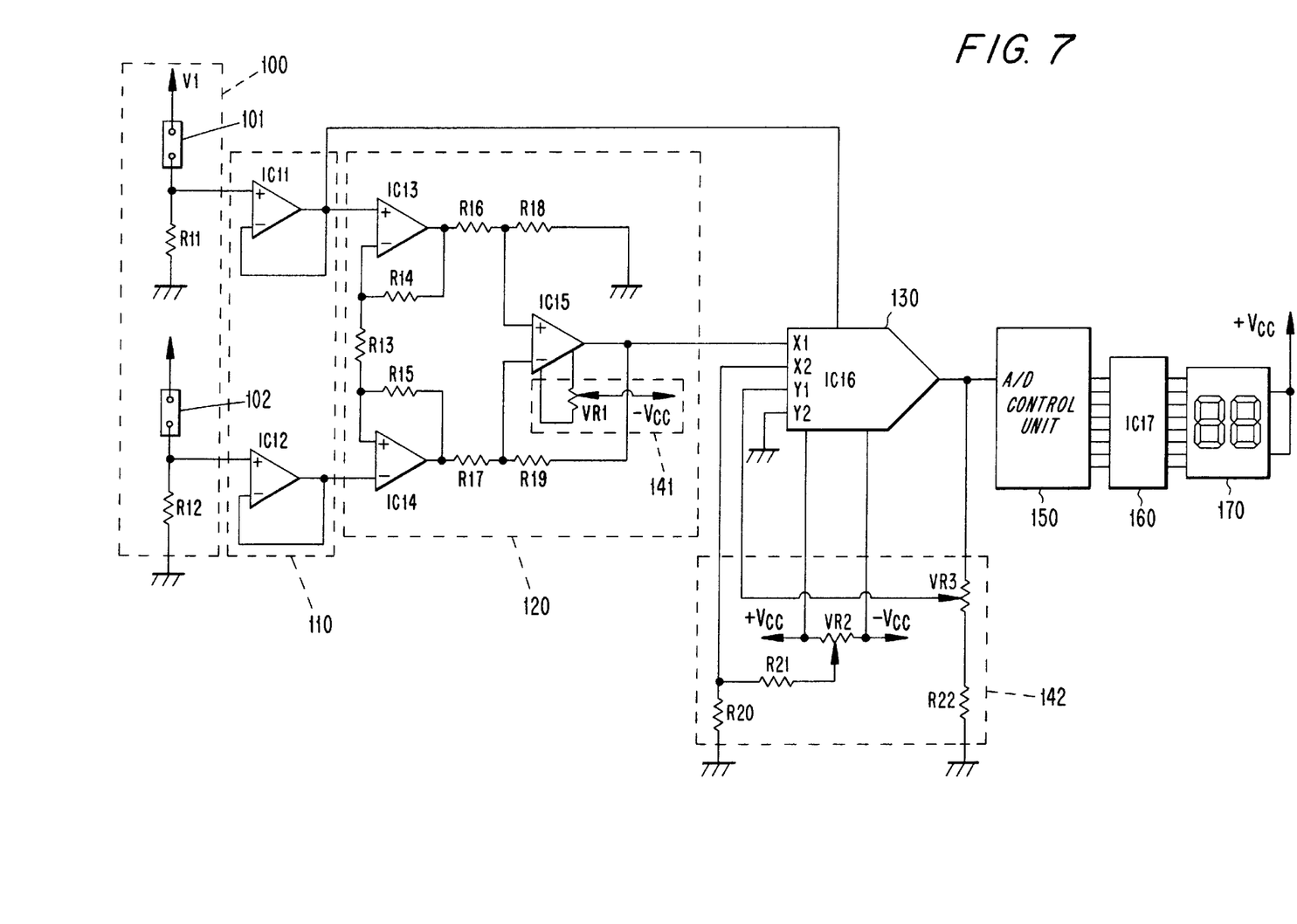
FIG. 7 is a detailed circuit diagram of FIG. 6.

FIG. 7 illustrates a circuit diagram for displaying the purifying efficiency of the water purifier according to the preferred embodiment. A coupling point between the water supply quality sensing element 101 and a resistor R11 having its one end grounded is connected to a non-inverting terminal of IC11 of the amplifying means 110, another coupling point between the produced water quality sensing element 102 and a resistor R12 having its one end grounded is connected to a non-inverting terminal of IC12 in the amplifying means 110.

The output of the IC11 is coupled into a non-inverting terminal of IC13 in the subtractor 120, the output of the IC12 is coupled into an inverting terminal of IC14. Both outputs IC13 and the IC14 are connected to IC15 of whose output is in turn connected to one input terminal X1 of IC16 (the divider 130), and the output of IC11 is also connected to the IC16.

A first adjusting element 141 is connected to IC15 in the subtractor 120 and substantially comprises a variable resistor VR1 that is provided for performing a fine adjustment for obtaining a correct result output of IC15. Similarly, the second adjusting element 142 is connected to IC16 in the divider 130 and substantially comprises a variable resistor VR3 that is provided for performing a fine adjustment for obtaining correct data from the IC16.

The divider 130 receives both the output of IC11 and the output of IC15 of the subtractor 120 and performs a division of those outputs. The result of the division is applied to the input terminal A/D. The control means 150 analyzes the signal input thereto and outputs the analyzed result to IC17 of the drive circuit 160. Then, IC17 sends the signals output from the control means 150 to the displaying means 170 for displaying the final results.

The reference symbols R13 to R22 and Vcc denote resistors and a power supply, respectively.

A commercial AC power supplied to the purifier from an AC power source block(not shown) is converted into a DC voltage at a voltage level required to drive the water purifier. Thus, the application of DC voltage activates the respective driving circuits and the control means 150, which enables the initialization of the water purifier.

The amount of water stored in the water tank 35 is determined using the water level sensors 34 and 39. The varying output voltage depending upon the water level is sensed by the sensors 34 and 39, and the control means 150 executes a comparison of the output voltages of a full and empty water sensors and the predetermined reference voltage. The control means 150 determines whether the amount of the water stored in the water tank 35 indicates an empty water level or not, and controls the purifier to maintain a constant level of water in the water tank 35.

When the water level of the water tank 25 is determined as being higher than the empty water level, the purifying operation is not necessary until the water level drops below the empty water level.

However, when it is determined that the water level of the water tank 35 has lowered below the empty water level, the control means 150 controls the water supply valve 57 to be opened so as to perform the purifying operation to supply purified water to the water tank 35.

Once the water supply valve 57 has been opened, fresh water, such as tap water, begins to be fed into the water supply pipe 25 through the connecting member 23 from the faucet 22. The control means 150 drives the pressure pump 59 so that a pressure for fresh water fed through the water supply pipe 25 and into the membrane 29 reaches a predetermined level.

The activated pressure pump 59 opens the water supply valve 57, thereby enabling fresh water to be fed into the water supply pipe 25 from the faucet 22 to pass the pre-processing filter 27, which results in the removal of various noxious pollutant substances such as chlorine components. Then, fresh water from the above pre-processing filter 27 is supplied to the membrane 29 through the water supply pipe 57.

The water from the pre-processing filter 27 is then introduced into the membrane filter 29 through the water supply valve 51 while being increased in pressure to a certain pressure by the pressure pump 57. While passing through the membranes of the membrane filter 29, the water becomes free of heavy metals, bacteria, cancer-causing materials, and the like, contained therein.

The water emerging from the membrane filter 29 then passes through the post-processing filter 31 by which odorous substances such as noxious gas are removed from the water. The water from the post-processing filter 31 is then supplied to the water tank 35 through the water inlet port 33.

When the water level of the water tank 35, or the amount of the purified water introduced into the water tank 35 via the water inlet port 33, is sensed by the full and empty water level sensors 37 and 39 and corresponds to a full water level, the control means 150 blocks the water supply pipe 57 and stops the operation of the pressure pump 59 to constantly maintain the amount of the purified water in the water tank 35.

When the water purifier in accordance with the preferred embodiment is operated in such a manner as described above, the water in the water purifier is examined through the sensor 101, while the water emerging from the filters 27, 29 and 31 is examined through the sensor 102.

The signals having small amplitude from the sensors 101 and 102 are, respectively, applied to IC11 and IC12 of the amplifying means 110, and amplified. Then, the amplified signals are provided to the subtractor 120 having IC13 and IC14 in which the proper calculations are made as follows.

Assume that each of the symbols A, B and C represent the quality of the supply water fed to the water purifier, the quality of the water produced through the filters 27, 29 and 31, and the output result from the subtractor 120. The operation of the subtracter 120 yields the result C obtained by subtracting B from A.

However, in order to calculate a ratio of the removal of noxious pollutant substances of the produced water to the supply water, it is required to divide the result C from the subtractor 120 in accordance with an equation, i.e., C=A−B, into the data for the quality of the supply water used in the previous calculation. The following equation is derived: D=C/A (where D represents the division result). The divider 130 consisting of IC16 functions to calculate the above equation.

In the above-described processing, the first adjusting element 141 may be adjusted to obtain the correct result from the subtractor 120 through a fine adjustment for the element 141 made up of such as a variable resistor VR1. The fine adjustment for obtaining the correct data from the divider 130 is through the second adjusting element 142 made up of variable resistors VR2, VR3.

The result from the above divider 130 is applied to an input terminal A/D of the control means 150 which in turn supplies to its output the driving circuit 160, wherein the circuit 160 is composed of IC17, and displays the final result through the displaying means 170, such as 7-segment device.

A user who knows the pre-set value required to exchange a filter can determine whether the filter in the water purifier should be exchanged or not. The user may compare the data D of the divider 140 to the pre-set value for the exchange of the filters, and exchange the filters, in the case where the data D is less than the pre-set value after the above comparison.

Meanwhile, the control means 150 may control to display the purifying efficiency through the displaying means 170, or open a valve (not shown) for discharging the purified water in the water tank 35.

As described above, the present invention has merit in that the amounts of impurities in the supplied water and the purified water can be measured, accordingly, there can be provided a purifying efficiency to indicate what amounts of noxious pollutant substances are filtered through the filters, and it allows a user to know whether the filters are to be exchanged based upon the displayed purifying efficiency.

What is claimed is:

1. An apparatus for displaying the purifying efficiency of a water purifier having a set of filters including a pre-processing filter, a membrane filter, a post-processing filter, and a water tank for storing purified water passed through said filters, the apparatus comprising:

a supply water quality sensing element for sensing a first amount of pollutant substances contained in fresh water supplied to the purifier, and generating a first signal indicative of said first amount;

a produced water quality sensing element for sensing a second amount of pollutant substances contained in the purified water that has passed through said set of filters, and for generating a second signal indicative of said second amount;

amplifying means for amplifying the first signal and the second signal to generate a first amplified signal and a second amplified signal;

a subtractor for receiving the first and second amplified signals obtained from the amplifying means and deriving a difference signal indicative of a difference between the first and second amplified signals;

a divider for dividing the difference signal from the subtractor to produce a divided difference signal;

adjusting means for adjusting incorrect values of said divided difference signal;

control means for deriving a purifying efficiency based upon a signal output from the adjusting means and, from the derived result, outputting a quality signal indicating the purifying efficiency and a state of purification of the purified water; and displaying means for receiving the quality signal from the control means via a driving circuit and displaying the purifying efficiency and the purified state.

2. A circuit as claimed in claim 1, wherein each of the supply water quality sensing element and the produced water quality sensing element includes two metal sensing rods and means for sensing a flow of electric current between the rods to measure an amount of pollutant substances contained in the supplied water and the purified water, respectively.

3. A circuit as claimed in claim 1, wherein the amplifying means includes a first operational amplifier for amplifying the first signal generated by the supply water quality sensing element; and a second operational amplifier for amplifying the second signal generated by the produced water quality sensing element.

4. A circuit as claimed in claim 1, wherein the subtractor includes a first operational amplifier for receiving the first amplified signal for the supply water quality sensing element; a second operational amplifier for receiving the second amplified signal for the purified water quality sensing element; and a third operational amplifier for receiving the signals output from the first and second operational amplifiers.

5. A circuit as claimed in claim 1, wherein the control means causes contaminated water to be discharged from the water tank in accordance with an output signal from the divider.

6. A circuit as claimed in claim 1, wherein the displaying means is adapted to display information indicating whether the purified water is drinkable, which displaying means is controlled according to the control means.

7. A circuit as claimed in claim 1, further comprising adjusting means for adjusting incorrect values of said derived difference signal.

8. A method for assessing the efficiency of a water purifier, the method comprising the steps of:

sensing a degree of contamination in supply water supplied to the water purifier;

producing a first signal corresponding to the level of contamination of the supply water;

filtering the supplied water to produce purified water;

sensing a degree of contamination in the purified water produced by the filtering;

producing a second signal corresponding to the level of contamination of the purified water;

comparing the first signal with the second signal to derive a signal representative of the degree to which the supply water has been purified;

adjusting values of the derived signal during the comparing step; and displaying results of the comparing step.

9. The method claimed in claim 8, wherein the step of sensing a degree of contamination includes assessing the conductivity of water being sensed.

10. The method of claim 8, further comprising the step of discharging contaminated water from a water tank for storing purified water in accordance with the results of the comparing step.

* * * * *